United States Patent
Gentz et al.

(10) Patent No.: US 11,406,768 B2
(45) Date of Patent: Aug. 9, 2022

(54) ELECTRONIC MODULE FOR MONITORING INJECTION DEVICES

(71) Applicant: Ypsomed AG, Burgdorf (CH)

(72) Inventors: Michael Gentz, Burgdorf (CH); Ursina Streit, Schönbühl (CH); Marcel Derungs, Richterswil (CH); Leos Urbanek, Bern (CH); Daniel Burgener, Uster (CH); Jonas Rihs, Pieterlen (CH)

(73) Assignee: Ypsomed AG, Burgdorf (CH)

( * ) Notice: Subject to any disclaimer, the term of this patent is extended or adjusted under 35 U.S.C. 154(b) by 259 days.

(21) Appl. No.: 16/363,652

(22) Filed: Mar. 25, 2019

(65) Prior Publication Data
US 2019/0217022 A1  Jul. 18, 2019

Related U.S. Application Data

(63) Continuation of application No. PCT/CH2017/050004, filed on Sep. 26, 2017.

(30) Foreign Application Priority Data

Oct. 3, 2016  (CH) .................................... 01306/16

(51) Int. Cl.
| | | |
|---|---|---|
| *A61M 5/32* | (2006.01) | |
| *A61M 5/20* | (2006.01) | |
(Continued)

(52) U.S. Cl.
CPC .............. *A61M 5/326* (2013.01); *A61M 5/20* (2013.01); *A61M 5/3129* (2013.01);
(Continued)

(58) Field of Classification Search
None
See application file for complete search history.

(56) References Cited

U.S. PATENT DOCUMENTS

| | | | |
|---|---|---|---|
| 7,078,679 B2 * | 7/2006 | Westphall | ............. H01J 49/027 250/288 |
| 10,195,352 B2 | 2/2019 | Baran et al. | |

(Continued)

FOREIGN PATENT DOCUMENTS

| | | |
|---|---|---|
| EP | 2065064 A1 | 6/2009 |
| EP | 2182456 A1 | 5/2010 |

(Continued)

OTHER PUBLICATIONS

PCT, "International Preliminary Report on Patentability", Application No. PCT/CH2017/050004, dated Apr. 9, 2019, 6 pages.

(Continued)

*Primary Examiner* — Jenna Zhang
(74) *Attorney, Agent, or Firm* — Dorsey & Whitney LLP

(57) ABSTRACT

The invention is concerned with a simple and reliable manner of monitoring a handling or use of injection devices by means of a reusable electronic module. According to the invention, a displacement of a component of the injection device between an initial position and an intermediate position, and a subsequent displacement of the same component between the intermediate position and a final position essentially identical with the initial position is observed by one and the same sensor comprised in an electronic module separate from the injection device. A status or state of the injection device is then inferred in the electronic module from these two observations by way of digitally processing sensor output information. The invention thus enables secure, easy and cost-effective operation of components, devices and systems for the generation, collection and distribution of data associated with the handling or use of the injection devices.

19 Claims, 6 Drawing Sheets

(51) Int. Cl.
  *A61M 5/31* (2006.01)
  *A61M 5/315* (2006.01)

(52) U.S. Cl.
  CPC ........ *A61M 5/3157* (2013.01); *A61M 5/3243* (2013.01); *A61M 2005/3142* (2013.01); *A61M 2205/3317* (2013.01)

(56) References Cited

U.S. PATENT DOCUMENTS

| | | | |
|---|---|---|---|
| 2008/0169307 A1 | 7/2008 | Hofstetter | |
| 2008/0188813 A1* | 8/2008 | Miller | G01D 21/00 604/207 |
| 2011/0270214 A1* | 11/2011 | Jorgensen | A61M 5/31551 604/207 |
| 2011/0288523 A1* | 11/2011 | Donovan | A61B 17/8872 604/500 |
| 2011/0295215 A1* | 12/2011 | Nielsen | G16H 20/17 604/257 |
| 2011/0313350 A1* | 12/2011 | Krulevitch | G16H 20/17 604/65 |
| 2014/0379874 A1 | 12/2014 | Starr et al. | |
| 2015/0025470 A1 | 1/2015 | Baran et al. | |
| 2015/0202375 A1* | 7/2015 | Schabbach | G16H 20/17 604/207 |
| 2015/0273163 A1 | 10/2015 | Nielsen et al. | |
| 2015/0290396 A1 | 10/2015 | Nagar et al. | |
| 2016/0129182 A1 | 5/2016 | Schuster et al. | |
| 2016/0213853 A1 | 7/2016 | Despa et al. | |
| 2017/0146381 A1* | 5/2017 | Eckel | A61M 5/31535 |
| 2017/0232203 A1* | 8/2017 | Krusell | A61M 5/24 604/207 |
| 2018/0200451 A1* | 7/2018 | Shekalim | A61M 5/31525 |
| 2018/0225560 A1* | 8/2018 | Schneider | G06K 19/07773 |
| 2018/0280624 A1* | 10/2018 | Bitton | A61M 5/3155 |
| 2018/0326164 A1 | 11/2018 | Bauss et al. | |
| 2019/0001060 A1 | 1/2019 | Gylleby et al. | |
| 2019/0255252 A1 | 8/2019 | Gentz et al. | |
| 2019/0365989 A1 | 12/2019 | Allerdings | |

FOREIGN PATENT DOCUMENTS

| | | |
|---|---|---|
| EP | 2781230 A1 | 9/2014 |
| WO | 2010098927 A1 | 9/2010 |
| WO | 2014023763 A1 | 2/2014 |
| WO | 2015136564 A1 | 9/2015 |
| WO | 2015171778 A8 | 12/2015 |
| WO | 2016102407 A1 | 6/2016 |
| WO | 2018085952 A1 | 5/2018 |

OTHER PUBLICATIONS

PCT, "International Search Report and Written Opinion", Application No. PCT/CH2017/050006, dated Feb. 5, 2018.
PCT, "International Search Report and Written Opinion", Application No. PCT/CH2017/050004, dated Jan. 31, 2018, 10 pages.
"Choosing Hand Tools; What is My Hand Size?" retrieved from http://choosehandsafety.org/choosing-hand-tools/hand-tool-size retrieved on Feb. 10, 2021.

\* cited by examiner

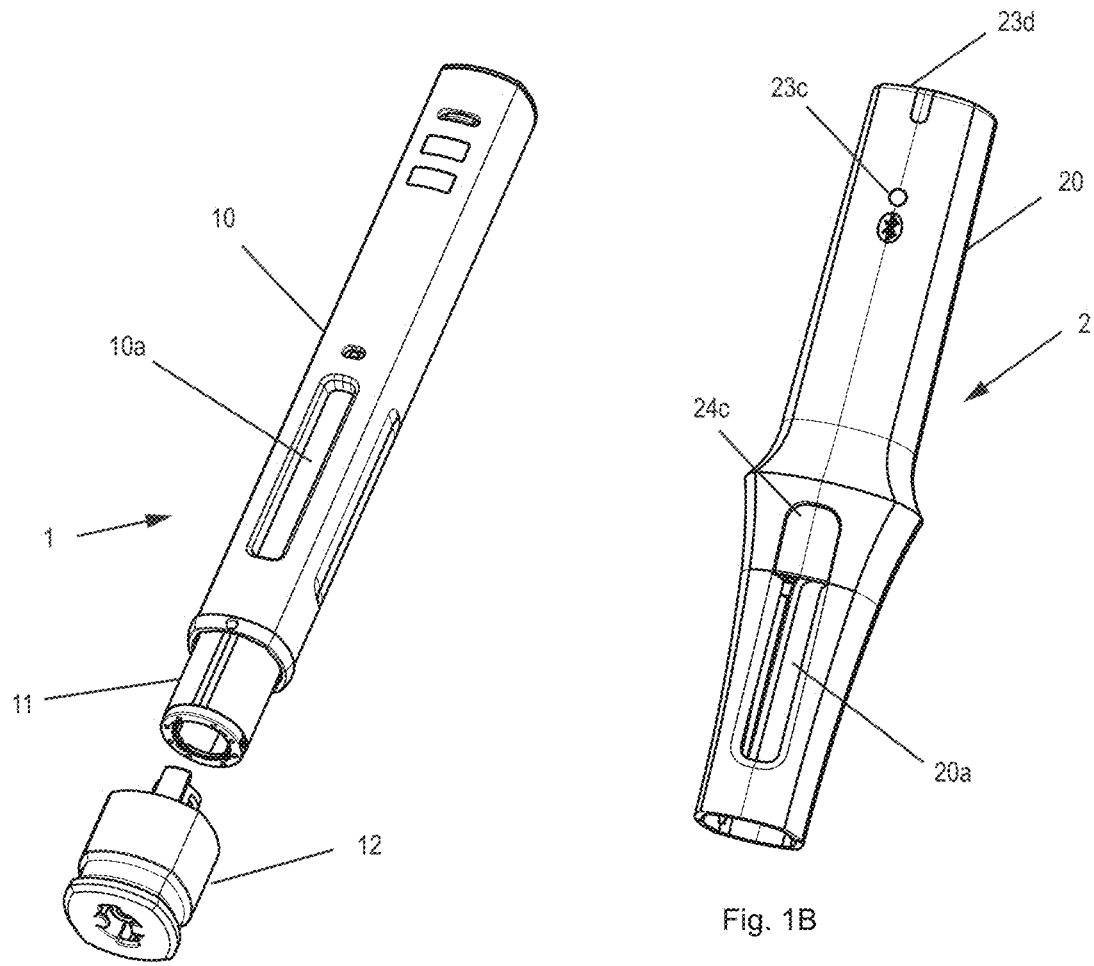
Fig. 1A
Fig. 1B
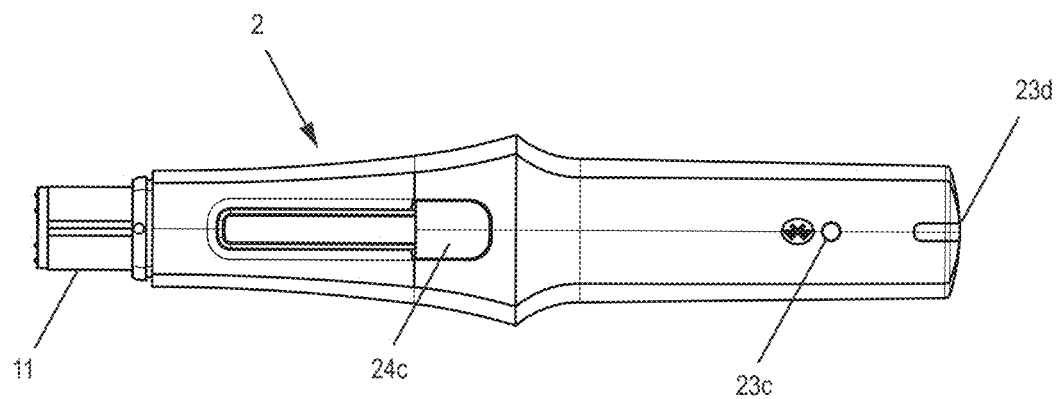
Fig. 1C

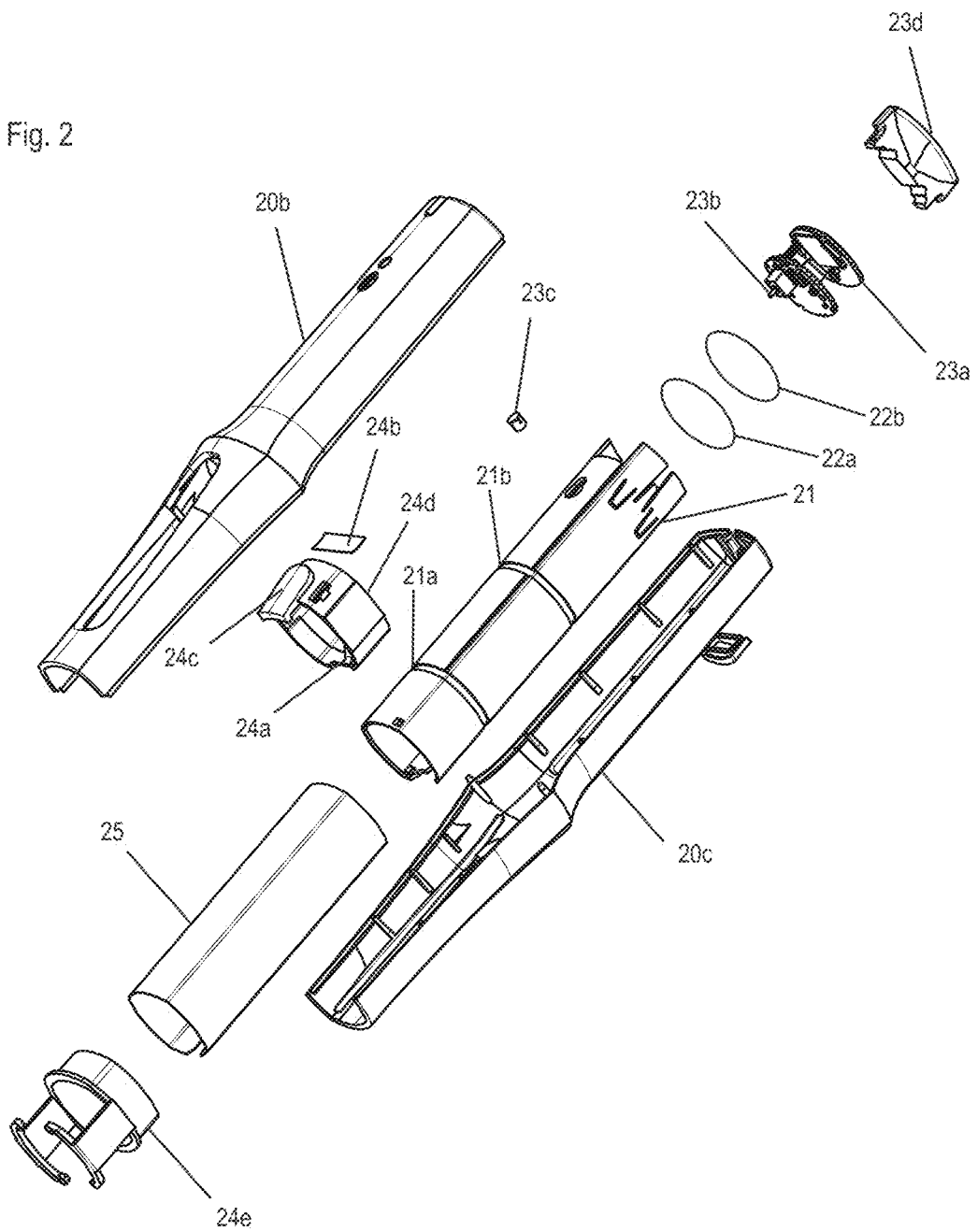

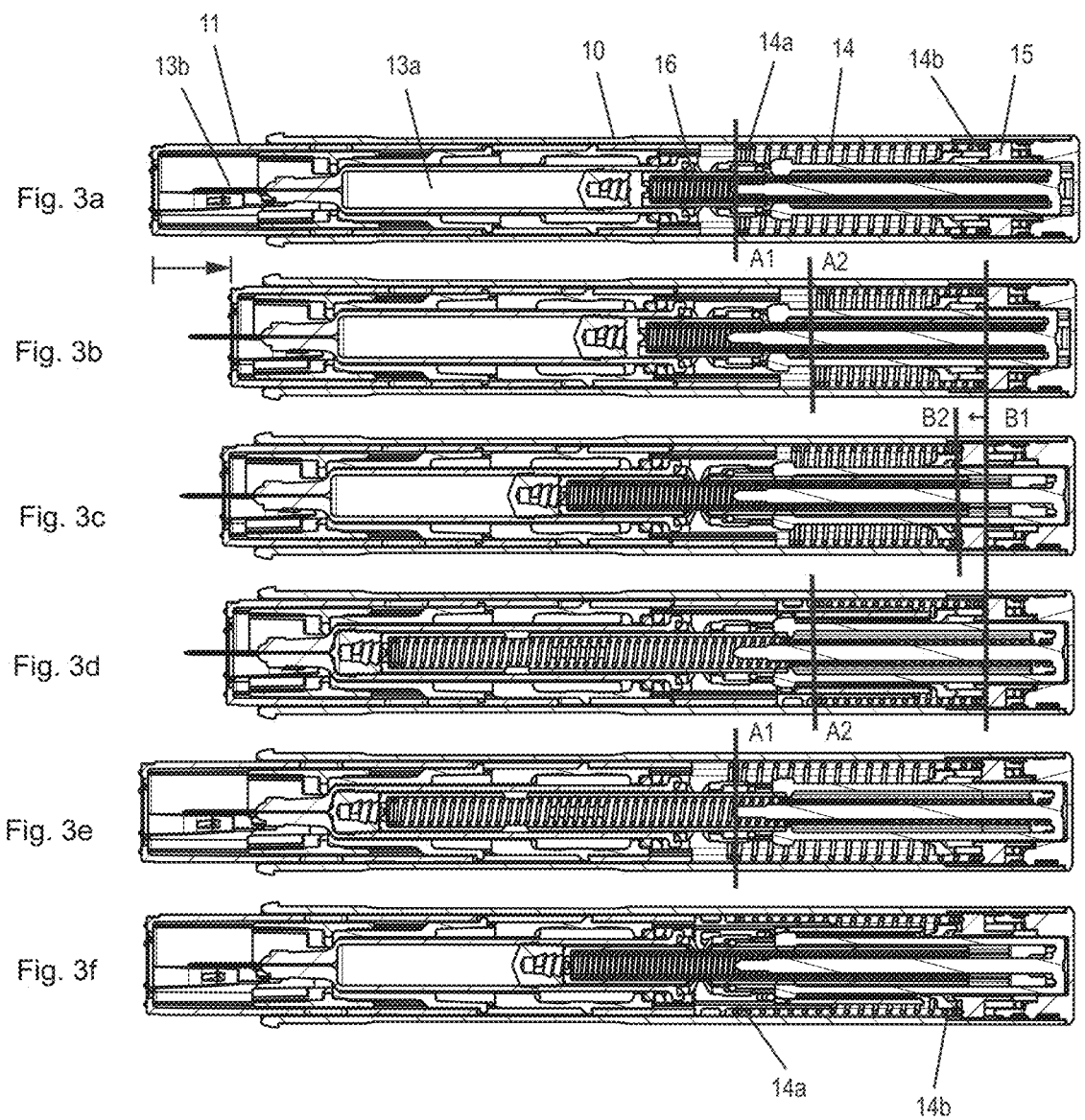

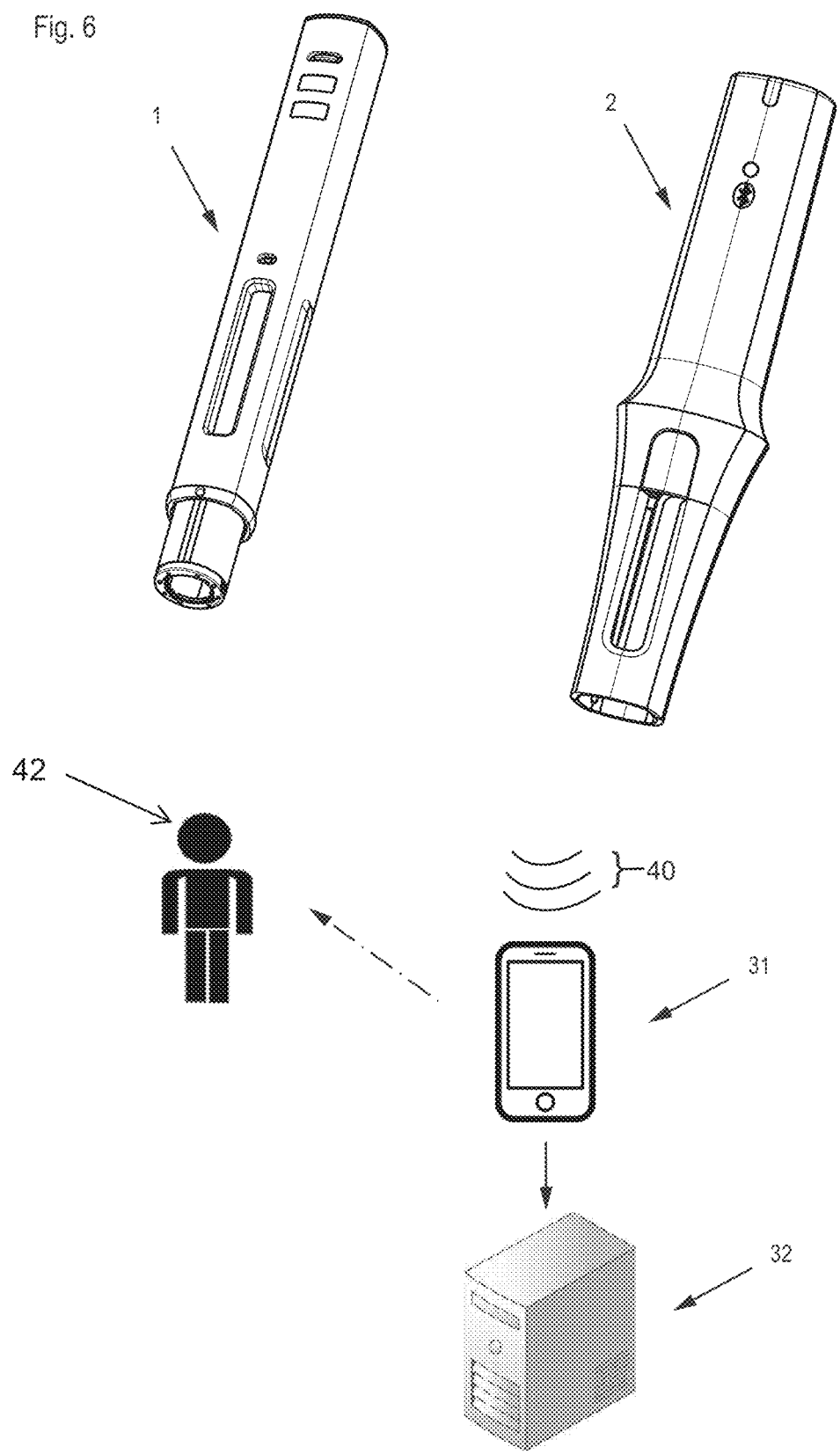

ELECTRONIC MODULE FOR MONITORING INJECTION DEVICES

CROSS-REFERENCE TO RELATED APPLICATIONS

This application is a continuation of International Application No. PCT/CH2017/050004 filed Sep. 26, 2017, which claims priority to Swiss Application No. 01306/16 filed Oct. 3, 2016, the entire contents of all of which are incorporated by reference herein in their entirety.

FIELD OF THE INVENTION

The present invention relates to injection devices or medicament delivery devices for injecting, delivering, administering, infusing or dispensing substances and/or liquids such as insulin or hormone preparations. It departs from a medical monitoring system with an injection device and an electronic module attachable to the injection device.

BACKGROUND

WO 2016/102407 discloses a drive unit for a drug delivery device of a linear actuator type, with a stator comprising a plurality of coils arranged in axial direction around a movable armature, the armature in turn comprising a number of magnets. An axial position of the armature is determined from the inductances of the coils, in particular by locating the one coil with an inductance differing from all the other inductances. The drive unit serves for both driving the armature and determining its axial position such that no further sensor is required.

US 2008169307 discloses a dose setting module for use with an injection device, the module including sensor elements and at least one sensor actuating element that can be rotated in a circumferential direction of the injection device to cause a change in the magnetic field generated by a sensor element. The sensor actuating element is disposed on a threaded rod of the dose setting mechanism. An evaluation unit connected to the sensor element emits a first or second signal depending on a detected change in the magnetic field.

WO 2014/023763 discloses a supplemental device for attachment to an injection device, with an inductive sensor arranged to detect movement of a drive screw of the injection device during medicament delivery. The drive screw of the injection device is specifically adapted and provided with a pattern of magnetic material or magnetic coating on a surface thereof. Inductive sensors, such as Hall sensors or coils of conductor, detect movement of the magnetic markings inducing an electric potential in the sensor. The pattern of the signals provided may be unique for each location on the drive screw.

The above prior art approaches focus on a detection of a set dose or of an expelled dose in variable-dose injection devices and in general do require significant adaptations to the injection device. This specifically holds for configurations as in WO 2014/023763 where a reusable electronic module attaches to a disposable mechanical injection device in a releasable or removable way. In such a configuration, there are no sensors comprised in the injection device for preparing and digitally processing sensor output information about the operation of the injection device, and there is no communication interface provided for conveying such information to an information subscriber. Accordingly, the sensors comprised in the electronic module are at a certain distance from any sensor actuator comprised in the injection device, and the sensor actuator has to be adapted specifically in order to generate primary signals that are readily detectable outside of the injection device. Potential adaptations to the injection device in this context include designing of openings in the housing to allow for visual inspection, reverting to specific, e.g. magnetic, materials on movable components of the injection device for continuous component tracking, or providing extra sound generating means for acoustical event recording.

EP 2781230 discloses an exemplary disposable injection device in the form of an auto-injector for automatically injecting an active agent or a drug. The auto-injector has an elongate casing including a syringe holder part for accommodating an active agent container or pre-filled syringe with an injection needle at a distal (or forward) end. A driving spring is provided for biasing a piston rod and shifting a piston comprised in the container in order to deliver the active agent. The auto-injector also includes a needle protective sleeve or tube that surrounds the needle in a first position, and that may be axially moved in a proximal direction towards a second position. When the distal end of the auto-injector is pressed onto the skin of a patient the needle protective sleeve is displaced in a proximal direction, and a needle protective sleeve spring is charged or tensioned. An end-click element is displaced in a distal direction by means of the relaxing injection spring, which in turn causes an additional tensioning of the needle protective sleeve spring. At the end of an injection, the end-click element is released to move in proximal direction under the effect of the needle protective sleeve spring until it abuts and generates an end-click. Accordingly, the movements, or rather the position, of the end-click element, or click sleeve, may be mechanically detected by a position switch interacting with the click sleeve through an opening in the device housing.

SUMMARY OF THE INVENTION

It is an objective of the invention to monitor, in a simple, reliable manner and by means of a reusable electronic module, a handling or use of injection devices for administering a medicament. It is a further objective of the invention to enable secure, easy and cost-effective operation of components, devices and systems for the generation, collection and distribution of data associated with the handling or use of the injection devices.

According to the invention, a displacement, or movement, of a component of the injection device between an initial position and an intermediate position, and a subsequent displacement of the same component between the intermediate position and a final position essentially identical with the initial position is observed by one and the same sensor comprised in an electronic module separate from the injection device. A status or state of the injection device is then inferred in the electronic module from these two observations by way of digitally processing sensor output information. In fact, sophisticated detection of a dose setting or ongoing dose delivery is not imperative, and an injection process may already be monitored to a sufficient extent based on a detection of distinct steps that correspond to a back and forth movement of a single device component. The component to be displaced serves as an actuator generating, in the two component positions, a primary signal that may be readily detected by a suitable sensor placed in proximity to both component positions.

The invention may be advantageously employed for monitoring a use or handling of fixed dose injection devices, including single-dose injection devices such as auto-injectors or patch injectors as well as multi-dose injection devices such as spring driven autopens or fixed dose injectors, for which there is neither a need nor a possibility to detect dose settings or injected dose quantities. Additionally or alternatively, the invention may be used to advantage in configurations where a reusable electronic module attaches to a disposable mechanical injection device in a releasable or removable way, specifically in retrofit configurations with an existing injection device design that is not available for adaptations as described above and focusing on the generation of detectable primary signals. Injection device properties focusing on other kinds of interaction between the electronic module and the injection device may independently be present or be excluded. For instance, a mechanical keying element of the electronic module may interact with dedicated counterpart keying element provided on the injection device to disable activation preventing elements of the injection device, and as a prerequisite for a proper use of the injection device.

In a first aspect of the invention, an injection process is monitored by means of inductive sensing equipment provided in an electronic module for detecting two-way, or reciprocating, displacements of a component of the injection device. Specifically, a medical monitoring system comprises an injection device or drug delivery device such as an auto-injector with a device housing. The system further comprises a reusable electronic module or electronic unit with a module housing and adapted to be removably, or releasably, attached to the injection device for monitoring of an injection process executed by a user by means of the injection device. The electronic module comprises an inductive sensor for detecting, in an attached state of the electronic module and the injection device, initial, intermediate, and final values of, and/or corresponding changes or differences in, a static or alternating magnetic field or flux. The magnetic field or flux differences are caused by a first displacement of a component of the injection device from a first to a second position of the component, and by a second, subsequent, or return displacement of the component from the second to the first position of the component.

In a first preferred embodiment of the first aspect of the invention, the inductive sensor comprises a sensor for detecting a static magnetic field, such as a Hall sensor or a magneto-resistive sensor, and the component is at least partially made of permanent magnetic material producing, in both the first and second component position, a static, i.e. non-alternating magnetic field of sufficient intensity to be detected by the sensor.

In an alternative first preferred embodiment of the first aspect of the invention, the inductive sensor comprises an induction coil and the component to be displaced is a conductive component at least partially made of electrically conductive material permitting the flow of alternating currents that produce an alternating magnetic field of sufficient intensity to be detected by the induction coil in both component positions. Initial, intermediate, and final values of, and/or corresponding changes or differences in, a mutual inductance or coupling between induction coil and component in the two component positions may thus be determined. This embodiment relies on suitable conductors readily available in existing injection device designs, including metallic springs for at least one of piston forward, syringe forward or retraction, cover sleeve retraction or forward, click sound generation, component securing or component locking, or including metallic shields for mechanical reinforcement e.g. as part of the cap remover, or including other metallic components such as rods, knobs, and wheels. Hence, this embodiment specifically works with injection devices devoid of any kind of permanent magnetic material, and obviates a dedicated provision of permanent magnets to an existing injection device design.

In somewhat more detail, an alternating current flowing in the induction coil will generate an alternating magnetic or electromagnetic field that will induce an eddy current on the surface of a conductive component brought into the vicinity of the inductor. The eddy current generates its own magnetic or electromagnetic field, which opposes the original field generated by the induction coil as in a set of coupled inductors. Such coupling is a function of the resistivity, distance, size, and shape of the conductive component, and can be modeled as a distance dependent resistance and inductance on the primary side driving the induction coil. The equivalent LC circuit may then be oscillated, or stimulated, with an AC current of a variable operating frequency between 1 kHz and 10 MHz, and a resonant frequency of the LC circuit may be determined therefrom. Alternatively, any component made of a material capable of interacting with the induction coil in a component position-dependent manner may also serve the purpose. In particular, non-conductive magnetic materials including ferrites or paramagnetic materials may impact an inductance of the induction coil and result in a damping or change of resonance frequency of an LC circuit including the induction coil. On the other hand, a voltage or EMF induced by a permanent magnet moving in the vicinity of the induction coil may be less reliable and reproducible than the position-dependent evaluation proposed here.

In a second preferred embodiment of the invention, the injection device comprises a metallic cover sleeve spring coupled to a cover sleeve, or needle guard sleeve, which is movable between a first, or initial, cover sleeve position in which the cover sleeve laterally surrounds a needle of the injection device and a second, or operational, cover sleeve position in which the cover sleeve exposes the needle. The cover sleeve spring has a first base at a first, or distal, end with a winding forming a closed loop that is rigidly, or non-elastically, coupled to the cover sleeve. The first base of the cover sleeve spring serves as the conductive component, and the inductive sensor includes a first inductive sensor with a first induction coil arranged close to the first end of the cover sleeve spring and adapted to detect a first displacement of the first base of the cover sleeve spring corresponding to a retracting movement of the cover sleeve between the first and a second cover sleeve position, and a second displacement of the first base of the cover sleeve spring corresponding to a forward movement of the cover sleeve from the second cover sleeve position to the first cover sleeve position. The detected cover sleeve movements are indicative of the injection device being brought in contact with and being lifted off the skin of the patient, and may be advantageously combined with an End-of-Injection signal detection to obtain a useful characterization of the ongoing injection process.

In this embodiment, the induction coil may comprise an induction winding or loop defining a first sensor area, and a winding of the spring base of the cover sleeve spring as the conductive component may form a closed conductor loop defining a second sensor area, or sensor actuator area, such that the relative arrangement of the two sensor areas gives rise to a detectable mutual inductance. Specifically, the spring base may include a first helical winding with an electrical contact between a first turn of the winding and a second, adjacent winding turn at a point of overlap, permitting the flow of circular currents. Such a closed conductor winding or loop with induced currents circulating around a well-defined second sensor area is preferred over other, i.e. non-loop conductor topologies that only permit the flow of eddy currents on the surface of the conductor. In addition, and although requiring adaptations to the injection device, an auxiliary washer disk may be provided at the spring base to reinforce the effect.

In another preferred embodiment, the injection device comprises an End-of-Injection (EoI) signaling assembly with an end-click member and a resilient member which is charged, or tensioned, in a preparatory movement at or near the start of the injection process, and which is discharged in a signaling movement at or near the end of the injection process in order to signal completion of a substance expel or piston forward activity. The signaling movement includes releasing the resilient member and moving the end-click member under the effect of the resilient member to abut a stationary component of the injection device and to generate an end-click. A member of the EoI signaling assembly, i.e. the resilient member, the end-click member, or an auxiliary conductive washer member, serves as the conductive component, while the inductive sensor includes a second inductive sensor with a second induction coil arranged close to the EoI signaling assembly and adapted to detect a preparatory movement of the EoI signaling assembly between a first position and a second position of the EoI signaling assembly, and adapted to detect the signaling movement of the EoI signaling assembly between the second and the first position of the EoI signaling assembly. The detected EoI signaling assembly movements are indicative of a start and an end of a substance delivery, and may be advantageously combined with an injection device lift-off signal detection to obtain a useful characterization of the ongoing injection process.

In a further preferred embodiment of the invention, the resilient member is identical with the cover sleeve spring, with a second base at a second, or proximal, end of the cover sleeve spring being rigidly coupled to the end-click member. The second base includes a winding forming a closed conducting loop that serves as the conductive component. The inductive sensor is a second inductive sensor with a second induction coil arranged close to the second end of the cover sleeve spring and adapted to detect a first displacement of the second base of the cover sleeve spring corresponding to a preparatory movement of the end-click member between a first position and a second position of the end-click member, and a second displacement of the second base of the cover sleeve spring corresponding to a signaling movement of the end-click member between the second and the first position of the end-click member. Incidentally, the additional statements about the induction coil and spring base properties made above in connection with the second preferred embodiment also apply to this further preferred embodiment.

In a next preferred embodiment, the inductive sensor comprises an induction coil surrounding the injection device in a sensor plane perpendicular to a main axis of the injection device, which assures optimal inductive coupling, or largest mutual inductivities, in a sensor arrangement involving the base of a cover sleeve spring that is parallel to, or co-planar with, the sensor plane. Alternatively, the induction coil may be arranged on a planar or even curved, e.g. cylindrical, surface that in turn is mounted coaxial with, or parallel to, the main axis.

In another advantageous variant of the invention, the electronic module comprises a wireless unit for communicating with a mobile device such as a smartphone, and a visual, audible and/or tactile status indicator indicating to a user a status of the system. The status of the system may include any of a device status of the injection device, a module status of the electronic module, or a process status of an overall injection process or injection device handling process. The status indicator may be simple and limited to a few Light Emitting Diodes (LEDs) in traffic-light colors and/or an audible signal generator for generating language-independent beep sounds or simple melodies, in particular in case of a mobile device with elaborate graphic display and speech output capabilities being communicatively connected to the electronic unit. The status information may be redundant or complementary to primary signals from the injection device that a user may still capture in parallel. In particular, the status information includes a lapse of a minimum holding or delay time of typically a few seconds following completion of a substance expel or piston forwarding activity, to inform the user that it is now safe to remove the injection device.

In another advantageous variant of the invention, the electronic module comprises a magnetic shield for shielding the inductive sensor against a source of electromagnetic interaction with the inductive sensor other than the moving component. Where the moving component includes a conductive base of a cover sleeve spring, the magnetic shield comprises a tubular sleeve embedded in the electronic module and surrounding the induction coil of the inductive sensor that interacts with the spring base. The magnetic shield may be made of a sheath of ferrite or any other high permeability material adapted to the operating frequency of the inductive sensor.

In another advantageous variant of the invention the electronic module comprises a locking mechanism with a release button for releasably locking or fixing the electronic module axially to the injection device. Where the device housing has a cylindrical surface that is not rotationally symmetric around a device main axis but exhibits, e.g., a rounded square cross section perpendicular to the main axis, the locking mechanism may be exclusively axial and hence devoid of a rotational locking component.

In another preferred embodiment of the invention the injection device housing or casing is elongate and the electronic module housing has a cavity adapted to the device housing such that, in the attached state, the electronic module essentially surrounds the injection device over at least a proximal, or rear, half of the elongate injection device housing, and preferably over at least three quarters of an overall length of the injection device. Accordingly, the user exclusively seizes and holds the module housing and not the device housing in the attached state, which requires a reliable locking mechanism with a lock against axial movement of the module relative to the injection device, specifically during removal of the needle protective cap and during needle insertion. The elongate module housing may be designed to increase usability and provide a better grip by shaping the external surface in a convex manner with distal and/or proximal housing parts of increased diameter to facilitate a transfer of axial force from the user to the device. Ultimately, an elongate module housing extending, in the attached state, over a substantial part of the length of the injection device is a prerequisite for placing the first inductive sensor in proximity to the first, distal, base of the cover sleeve spring.

In short, an electronic module according to the invention, comprising a module housing and being adapted to be removably attached to an injection device with a device housing, for monitoring of an injection process executed by means of the injection device, is characterized by an inductive sensor comprising a sensor induction coil and a sensor control unit for detecting, in an attached state of the electronic module and the injection device, an inductance of the sensor induction coil which is dependent on a first and/or second position of a component of the injection device that is at least partially made of electrically conductive material. The electronic module may further be characterized in that the sensor control unit is configured to determine changes in the inductance of the sensor induction coil caused by a first displacement of the component from a first to a second component position and caused by a second displacement of the component from the second to the first component position. The electronic module may additionally incorporate any or all of the advantageous refinements discussed above.

In a second aspect of the invention, an injection process is characterized by two events that are detectable by a single sensor means as a two-way, back and forth displacement of a movable base of a cover sleeve spring of the injection device. The base of the cover sleeve spring may comprise base winding loops with a diameter adapted to the diameter of the cover sleeve, and hence radially close to a circumferential device housing and at minimum radial distance to a sensor means external to the injection device. Specifically, a method of monitoring an injection process executed by means of an injection device with a cover sleeve spring coupled to an end-click member of an End-of-Injection (EoI) signaling assembly comprises the steps of:

Attaching to the injection device an electronic module with second sensor means.

Detecting, by the second sensor means arranged close to a proximal end of the cover sleeve spring, a first displacement of a second, or proximal, base of the cover sleeve spring corresponding to a preparatory movement of the EoI signaling assembly between a first position and a second position, which displacement implies a supplemental charging of the cover sleeve spring in view of an EoI signal generation.

Detecting, by the second sensor means, a second displacement of the second base of the cover sleeve spring corresponding to a signaling movement of the EoI signaling assembly between the second and the first position.

Concluding, by the electronic module and based on time-stamped sensor output signals indicative of the detected first and second displacement, on a correct execution of the injection process, whereby an expected order and time delay of the sensor output signals represent only a necessary, but not a sufficient condition for a truly proper handling of the injection device.

In an advantageous variant of the second aspect, the injection process is characterized by a sequence of four events that are observable with only two sensor means arranged in two distinct locations as the back and forth displacement of a first and the second movable base of the cover sleeve spring of the injection device. The first base of the cover sleeve spring is provided at a first, or distal, end of the spring opposite to the second base, at which first end the cover sleeve spring is coupled to, and chargeable by, a cover sleeve movable between a first, or initial, position in which the cover sleeve essentially surrounds a needle of the injection device and a second, operational position in which the cover sleeve exposes the needle. The method of monitoring an injection process then comprises the further steps of:

Detecting, by first sensor means arranged close to a distal end of the cover sleeve spring, a first displacement of a first, or distal, base of the cover sleeve spring corresponding to a retracting movement of the cover sleeve between a first and a second cover sleeve position.

Detecting, by the first sensor means, a second displacement of the first base of the cover sleeve spring corresponding to a forward movement of the cover sleeve from the second cover sleeve position to the first cover sleeve position.

Concluding, by the electronic module and based on time-stamped sensor output signals from the first and second sensor means indicative of the detected first and second displacement of the two bases, on a correct execution of the injection process. In this case, a correct execution of the injection process is acknowledged if the sensor signals are received in the expected order, with a deviation therefrom being indicative of an injection abort or malfunction of the injection device or electronic module components.

In the following context, the term "injection device" refers to a generally pen-shaped device with an elongate device body defining a longitudinal main device axis. The term "distal end" refers to the end of the injection device where an injection needle is located, the term "proximal end" designates the opposite end thereof.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

BRIEF DESCRIPTION OF THE DRAWINGS

The subject-matter of the invention will be explained in more detail in the following text with reference to preferred exemplary embodiments as illustrated in the attached drawings, of which FIGS. 1A-1B disclose an injection device and an associated electronic module; FIG. 1C shows the latter fitted to the former.

FIG. 2 depicts some parts of the electronic module in an exploded view;

FIGS. 3a-3f depict a sequence of operational longitudinal section views of the injection device;

FIG. 6 depicts an extended monitoring system comprising an injection device and an associated electronic module combined with a mobile device and remote server.

For consistency, the same reference numerals are used to denote similar elements illustrated throughout the drawings.

DETAILED DESCRIPTION

Figures 4A, 4B:
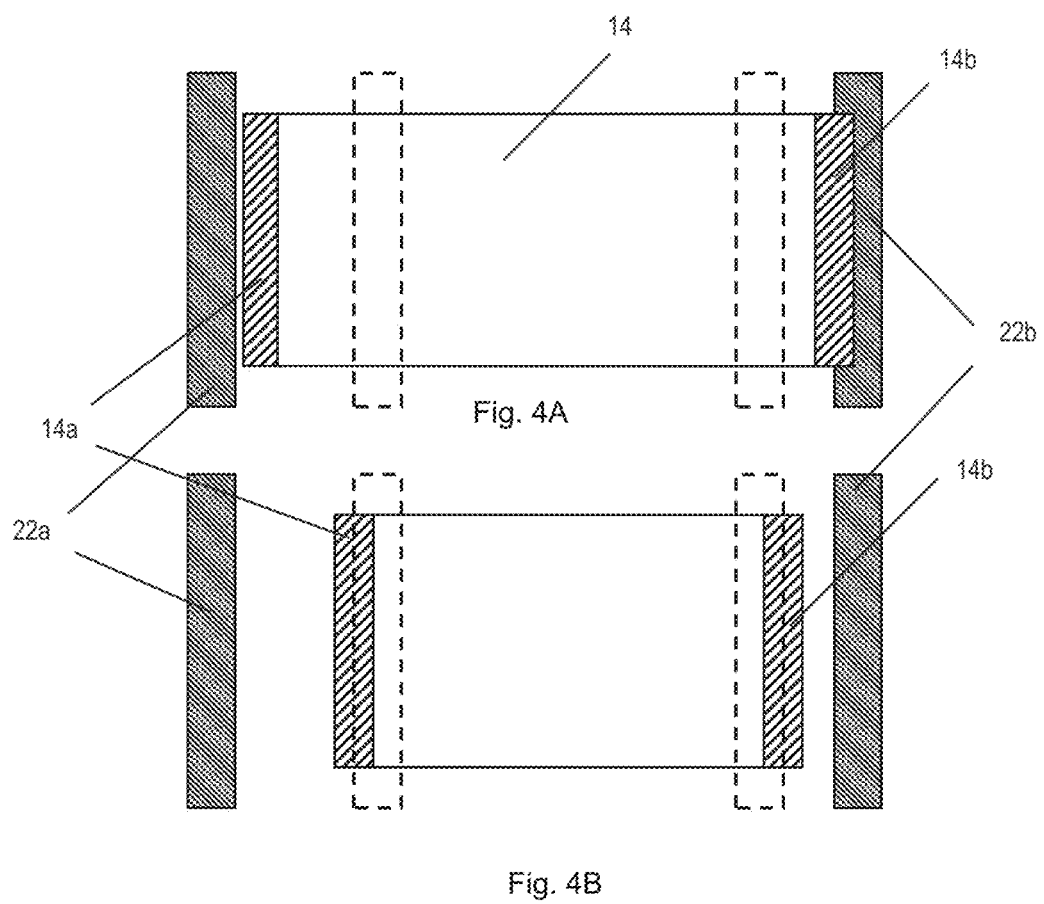
FIGS. 4A-4B depict schematically preferred relative arrangements of the sensor induction coils.

FIGS. 1A-1C depicts a monitoring system with an injection device 1 and an electronic module 2, both in a separated, or detached, state (top, FIGS. 1A-1B) and with the electronic module mounted, or attached, to the injection device (bottom, FIG. 1C). The injection device 1 has an elongate housing 10 essentially symmetric around a main axis, and a cover sleeve 11 that is movable between a first position (shown in FIG. 1A) and a second, or retracted, position in which the cover sleeve has moved in a proximal direction to be hidden inside, or enclosed by, the device housing. A needle protective cap 12 mounted onto a distal end of the injection device in order to protect, e.g. during shipping, a needle of the injection device has to be removed prior to injection, in order to expose the cover sleeve. The electronic module 2 has an elongate and hollow module housing 20 with a tubular sleeve forming a cavity or inner space adapted to an outer shape of the device housing, such that the injection device may be slidably inserted into the cavity. The module housing has openings 20a that match with windows 10a of the injection device, which in turn allow for visual inspection of a substance comprised in the injection device 1.

The electronic module further has a rear, or proximal, part where some or all electronic components as described below are located. Included in the module housing 20 is a lock/release mechanism to secure the attachment of the electronic module 2 to the injection device 1 in order to protect against unintended detachment, specifically during removal of the needle protective cap from the injection device. The lock/release mechanism includes a release button 24c for disengaging the electronic module 2 from the injection device 1. System status indicators 23c, 23d provide visual feedback about a connection status indicative of an established communication link 40 (see FIG. 6) to a mobile device 31, and about a device, module, or process status, including for instance an availability of battery power, a readiness of communication means, an attached/detached status of the electronic module and the injection device, or a progress of an ongoing injection process.

FIG. 2 depicts some parts of the electronic module 2 in an exploded view. The module housing comprises two housing parts, an upper cover 20b and a lower cover 20c, surrounding a sensor sleeve 21. The upper and lower cover provide a platform for individual designs of the module housing independent of the operational properties of the electronic module. A front, or distal, sensor induction coil 22a and a rear, or proximal, sensor induction coil 22b are mechanically supported by the sensor sleeve in corresponding circumferential recesses 21a, 21b, and electrically connected to other components of a suitable LC circuit as well as to sensor electronics comprised in an electronic assembly 23a that in turn is located in the rear part of the electronic module. The electronic assembly is further connected to a connection detection switch 23b to determine whether the injection device 1 has been fully inserted into the electronic module 2. The electronic assembly 23a includes a laterally arranged connection status indicator 23c in the form of an LED and light guiding means, and a proximally arranged system status indicator 23d in the form of an LED and light guiding means to provide visual signals indicative of a status of the injection device 1, of the electronic module 2, or of an ongoing, finished or aborted injection process.

A lock/release mechanism includes a locking element 24a in the form of a protrusion or nose engaging with a counterpart opening or recess of the device housing. The protrusion is biased by means of a locking spring 24b and connected to the release button 24c by way of a release button ring 24d that in turn is guided, or held, by a release button ring guide 24e, such that activating or pressing the release button 24c moves the protrusion out of engagement with the recess, against the force of the locking spring 24b. The cooperating opening preferably is a recess already existing in present device designs and possibly covered by a device label adhering to the device surface. Instead of the release button operated by pressing, a sliding element may be provided.

A magnetic shield 25 is provided as a tubular sleeve or sheet at least partially surrounding the sensor sleeve and sensor induction coils. Instead of a single component extending essentially over the complete length of the sensor sleeve as shown in FIG. 2, the magnetic shield may comprise two separate parts, each of which being centered around one of the induction coils 22a, 22b. The tubular sleeve may be open along a line parallel to the main axis, and produced by wrapping a foil without necessarily connecting the two edges of the foil facing each other along said line.

The electronic assembly 23a further includes microprocessor or microcontroller units suitably configured and physically mounted on Printed Circuit Boards, an antenna for wireless communication preferably according to the Bluetooth Low Energy BLE standard, and a power source or energy storage such as a battery. The microprocessor units may include a sensor control unit with an inductance-to-digital converter for preparing a digital sensor output signal, an evaluation unit for evaluating and consolidating sensor output signals from different sensors and/or with distinct time-stamps and for preparing augmented information, a data storage or event recording unit for storing dynamic injection process information as well as unique identification data of the electronic module and/or the user, and a communication unit for transmitting and receiving wireless signals via the antenna. The electronic assembly 23a may also include a timer and/or real time clock to provide absolute or relative clock information as needed for time-stamping of injection events or timing of a thermal equilibration process following retrieval of the injection device from a refrigerator.

Each induction coil may comprise between a few and several tens of turns, such as 30 turns, wherein the inductance and/or sensitivity increases with the number of turns. The two ends of the induction coil winding may be connected, as part of an LC circuit, resonator, or tank, to an Inductance to Digital converter such as the LDC 1612 or LDC 1614 of Texas Instruments as a COTS sensor control unit. The latter outputs a digital value indicative of the resonant frequency of the LC circuit in an exemplary frequency range between 1 kHz and 10 MHz that may further be converted to an equivalent inductance in the evaluation unit.

For the purpose of energy saving the connection detection switch 23b may act as an activation element capable of activating the electronic assembly from a power saving mode. In addition or alternatively, the power source or energy storage may be rechargeable, and to that end may include a USB connector, or be adapted for wireless power transfer from a docking station. The docking station may accommodate exclusively the electronic module, or the injection device together with the attached electronic module, and may be shared with other rechargeable electronic devices of a user, such as an electric toothbrush or a cordless phone. A smart docking station for the injection device may include additional functionality such as measurement of a temperature of the injection device and/or of the drug comprised in the syringe. If the injection device is placed in the smart docking station prior to use and after having been stored in a refrigerator, such temperature tracking performed by the docking station provides an acoustic and/or visual signal to the user as soon as the device temperature reaches a minimum administration temperature. During such initial thermal equilibration processes, the rechargeable energy storage of the electronic module may be recharged conveniently and without requiring further user intervention. The docking station may also deploy time and date information to start, adjust or synchronize a timer or a real time clock of the electronic module as well as user or therapy specific data.

FIGS. 3a-3f depict a sequence 3a to 3f of longitudinal sections of an injection device corresponding to successive operational steps as already described in EP 2781230. The injection device 1 has a device housing 10 and a syringe holder part for accommodating a pre-filled syringe 13a with a needle 13b at a distal end for dispensing or expelling a liquid. The injection device also includes a cover sleeve 11 that laterally surrounds the needle in a first (and final) position after removal of a needle protective cap as seen in views 3a, 3e and 3f. When the injection device is pressed onto an injection site the cover sleeve 11 is axially displaced in a proximal direction, i.e. in the direction of the horizontal arrow between views 3a and 3b. This retracting movement of the cover sleeve 11 is transferred to a rigid locking sleeve and further to a linear cover sleeve spring 14 that is compressively charged, strained or tensioned. An end-click element 15, or End-of-Injection ("EoI") signaling element, or click sleeve, is displaced in a distal direction by means of a relaxing injection spring 16, which in turn causes an additional compressive tensioning of the cover sleeve spring 14. At the end of an injection, the end-click element 15 is released to move in proximal direction under the effect of the cover sleeve spring 14 until it abuts and generates an end-click. Exemplary cover sleeve springs are made of conductive spring steel wire and have a length of 3 to 6 cm when assembled, a diameter of 1 to 2 cm and a total of 10 to 30 winding turns. Either spring base of the spring is formed by at least two winding turns electrically contacting each other in a direction of the device main axis over at least one revolution.

Views in FIGS. 3a to 3f depict in detail the various states of the injection device, starting with an initial state in view 3a in which the cover sleeve spring 14 is least charged or tensioned. View 3b depicts the state after insertion of the needle into the skin of a patient, with the cover sleeve 11 retracted and the cover sleeve spring 14 being compressed accordingly. The compression of the cover sleeve spring is represented by a displacement of a first base 14a of the cover sleeve between a first position (indicated by vertical line A1) and a second position (indicated by vertical line A2). View 3c depicts an ongoing drug expel or piston forward operation driven by the expanding injection spring 16. In an initial part of the injection spring expansion the EoI signaling component is displaced in distal direction by a small distance indicated by the horizontal arrow between views in FIGS. 3b and 3c. Correspondingly, a second base 14b of the cover sleeve spring 14 is displaced between a first position (indicated by vertical line B1) and a second position (indicated by vertical line B2). At the end of the drug expel operation, an end click is generated by the end-click element moving in proximal direction under the force of the expanding cover sleeve spring 14 to reach a final EoI signaling position as depicted in view 3d. After removal of the injection device from the injection site, the cover sleeve moves in distal or forward direction under the force of the expanding cover sleeve spring to reach a final (or initial) cover sleeve spring position as depicted in view 3e. Finally, view 3f depicts a status corresponding to an injection process interrupted before completion of the drug expel operation, with the first cover sleeve base 14a in the first position (A1) and the second cover sleeve base 14b in the second position (B2).

FIGS. 4A-4B depict schematically a preferred relative arrangement of the sensor induction coils 22a, 22b and the cover sleeve spring bases 14a, 14b, both in a more relaxed state of the cover sleeve spring 14 (FIG. 4A, top of sheet) corresponding to views 3a and 3e, and in a less relaxed state (FIG. 4B, bottom of sheet) corresponding to view 3c. Arranging the first sensor induction coil 22a at the distal side of the expanded, or first, position of the first cover sleeve spring base 14a (FIG. 4A, top of sheet) has the advantage that the signal detected is rather independent of the actual cover sleeve displacement or stroke. Preferably and as depicted in FIGS. 4A-4B for the first sensor induction coil 22a, a moderate axial gap between the sensor coil 22a and the expanded position of the cover sleeve spring base may be foreseen, to benefit from a highest sensitivity in terms of inductance change per unit of target displacement, and to exclude that despite some unavoidable manufacturing inaccuracies the maximum mutual inductance will be approached. Arranging the first sensor induction coil 22a at the proximal side of the compressed, or second, position of the first cover sleeve spring base (FIG. 4B, bottom, sensor coil position indicated in broken lines) is likewise possible. By analogy, the second sensor induction coil 22b may be arranged at a proximal side of the expanded position of the second cover sleeve spring base 14b (FIG. 4A, top) or at a distal side of the compressed position of the second cover sleeve spring base (FIG. 4, bottom, sensor coil position indicated in broken lines). On the other hand, placing the sensor induction coils in-between, particularly halfway between the two end positions of the respective cover sleeve spring bases 14a, 14b may not work properly.

Figure 5A:
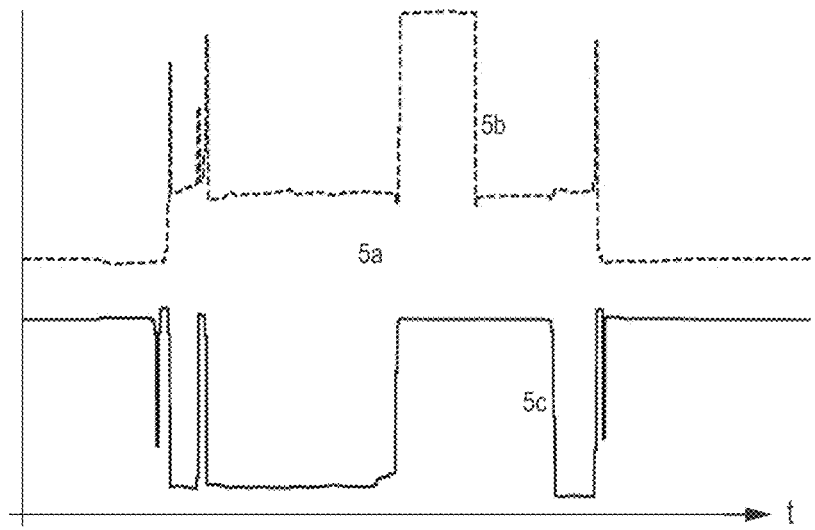
FIGS. 5A-5B each depict typical measured sensor output signals from two sensors in arbitrary units as a function of time.
Figure 5B:
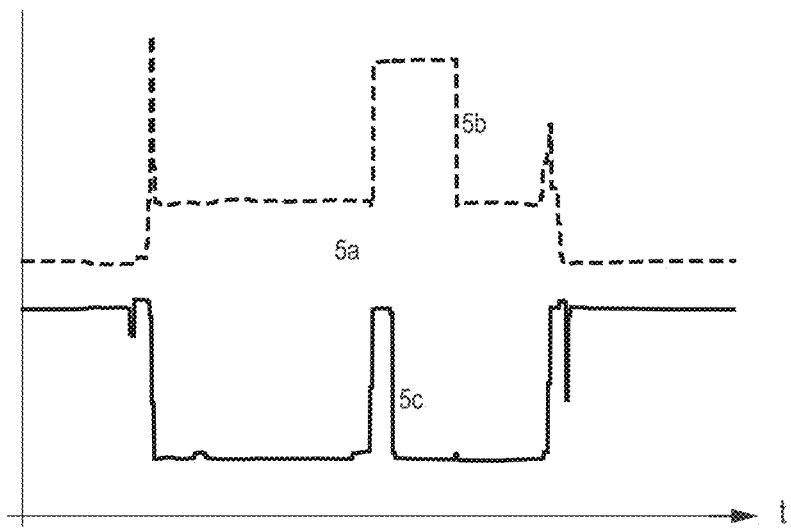

FIGS. 5A-5B depict typical measured sensor output signals in arbitrary units as a function of time, both in case of a correct injection (FIG. 5A, top) and in case of an interrupted or aborted injection (FIG. 5B, bottom). The sensor signals of interest in the present context include a distinctive first change of signal amplitude or level corresponding to a start of the drug expel operation with a quasi-simultaneous movement of both cover sleeve spring bases (event 5a) as unambiguously recorded by both of the two inductive sensors. At the end of the drug expel operation the End-of-Injection signaling component is activated by the moving second cover sleeve spring base (event 5b) and a change of signal amplitude is recorded by the second sensor induction coil and depicted by the broken line. A removal of the injection device from the injection site and corresponding displacement of the first cover sleeve spring base (event 5c) in turn is recorded by the first sensor induction coil as a change in signal amplitude back to the level prior to injection, as depicted by the continuous line. In the bottom graph (FIG. 5B) the order of the events 5b and 5c is reversed, from which an injection abort may be concluded. Likewise, a holding time abort may be concluded if the order of the two events is correct but a time delay between the two events is below a minimum holding time. The sensor signals are extremely reproducible and present very little noise. The uninteresting signals recorded prior to event 5a or after event 5c relate to the attachment/removal of the electronic module to/from the injection device. They may easily be suppressed by defining suitable measurement windows starting or ending with the connect status as determined by the connection detection switch.

FIG. 6 depicts an extended medical monitoring system with an injection device 1, electronic module 2, mobile device 31 capable of communicating with the electronic module, and an optional remote server, cloud based computing facility, or expert system 32. The electronic module 2 wirelessly transmits data about the injection progress via Bluetooth Low Energy (BTLE) or equivalent short or near range wireless communication technology (transmitted signal indicated at 40) to compatible mobile devices, e.g., at 31, such as smartphones and tablet devices running a dedicated app; or laptop computers and industrial readers configured accordingly. In case the mobile device is within reach of the user 42 and communicatively connected to the electronic module at the time of injection, such data upload may occur instantaneously during injection and include information about detected individual events or component movements. The data upload may also occur only following injection completion and include summary information about the entire injection instance. In the former case, the mobile device 31 may provide real-time Instructions for Use, guiding the user 42 through the successive steps of a single injection event.

In case no mobile device 31 is available at the time of injection, data upload is postponed, and real-time user support exclusively provided by means of the visual, audible and/or tactile status indicators of the electronic module 2. The data is locally stored in a data memory of the electronic module 2 until data upload to the mobile device 31 is possible, which may be the case only at a next injection, and which may occur both in an attached or detached state of the electronic module 2 and the injection device 1. Received injection data may be further conveyed from the mobile device 31 to external expert systems in order to individually assist patients, relatives, caregivers and healthcare professionals with customized information, and with an ultimate goal to improve patient adherence to a prescribed therapy plan. Accordingly, the mobile device 31 not only acts as a user interface providing information to a user 42 that mirrors or complements the status information generated by the electronic device itself, but also acts as a gateway to a cloud-based and secure data server and data evaluation facility. Alternatively, and particularly in case of an extended absence or unavailability of the mobile device 31, the data may be uploaded directly to a stationary receiver, for evaluation by an expert system and/or storage in a cloud computing environment. Such upload may take place by incorporating standard cellular mobile phone, e.g. GSM, or forthcoming low-power long range wireless communication technologies into the electronic module 2.

Exemplary data recorded by the electronic module 2 and subsequently or occasionally transmitted to the mobile device 31 for storage or further dissemination includes at least a timing and a quality information of an injection event. Basic timing information such as time and date may be complemented by an indication of the injection site, i.e. to which body part of the patient the drug has been injected. To that purpose the mobile device 31 may accept manually entering the injection site information, possibly along with a self-appraisal of patient well-being or therapy outcome. Basic quality information includes an indication whether the injection was performed correctly or whether a deviation occurred from the correct intended usage. In the latter case, the quality information preferably comprises an indication about the deviation observed, including an interruption of the injection as caused by removal of the injection device from the injection site during injection, or a short holding time as caused by removal of the injection device from the injection site before lapse of a holding time after drug expelling. ICT related information such as a network address or identifier of the injection device, the electronic module, and/or the mobile device as well as information on the communication network(s) employed by the mobile device 31 may be appended to the injection data at any stage of the transmission.

The mobile device 31 has to be set up initially by installing and configuring a smartphone application program and by duly identifying and enrolling the user 42, such as by means of a patient onboarding card conveying, by means of NFC or optical barcodes, all relevant data to the mobile device. The mobile device 31 may then provide assistance, support and/or guidance to the user 42, such as advising about counter measures in case a deviation is detected, informing the user about drug expiration dates, and providing interactive and/or animated instructions for use corresponding to all stages of the injection process. The complete injection process support may commence with a reminder function supporting the user 42 to remember when to perform an injection according to a prescribed therapy plan, continue with the timing of a thermal equilibration process following retrieval of the injection device from a refrigerator, a provision of instructions for attaching the electronic module and removing a needle protective cap from the injection device, suggesting an injection site, e.g. different from the last injection site, monitoring the drug administration, and end with a provision of instructions for detachment of the electronic module and disposal of the injection device. The electronic module 2 or the mobile device 31 may also notify the user 42 about an immediately preceding inactivity shut-down of the module, together with a warning that this may have led to the last injection process not having been registered correctly. The mobile device 31 may also store the data transmitted by the electronic module, specifically timing and a quality information of a sequence of injection events as a consolidated injection history, and occasionally forward this data to the optional remote server, cloud based computing facility, or expert system 32.

While the invention has been described above with reference to a particular type of automatic injection device, it is apparent to the skilled person that at least some of the benefits of the present invention may also be achieved in connection with a somewhat different injection device. In particular, patch injectors that are patched to the skin of the patient in view of a single dose injection taking between thirty seconds and several minutes likewise include displacing components that cause detectable magnetic flux changes. For instance, in addition to a piston being automatically moved distally to expel the dose, patch injectors also include a mechanism for automated needle insertion and retraction. Despite the fact that these two processes are driven by a source of electrical power the use of a separate electronic module may be advantageous in retrofit configurations with an existing patch injector design that is not available for the inclusion of sensors and electronics or for sourcing electrical power to the electronic module. Ultimately, fixed-dose injection devices that provide a limited number of fixed, non-variable injection dosage volumes for the user to choose from, and whether or not provided with electrical drive means, may also benefit from the invention.

Furthermore, an inductive sensor as described may also be used to detect a unidirectional movement of a magnetic or conductive component in view of a device status appraisal. For instance, an injection movement of a spring base of an injection spring driving a plunger and/or driving a syringe in a forward or retracting direction may be observed as well. Furthermore, and in particular in case of a spring driven initial syringe forward movement relative to the device housing, the cover sleeve may only be required to shield the needle once the injection device has been removed from the injection site. In this case, the cover sleeve spring may be pre-compressed, and the cover sleeve spring base may only perform a unidirectional relaxing movement to be detected by an inductive sensor.

While the housing of the electronic module is preferably mounted by sliding the module housing over the injection device, the module may be attached to the device in any other suitable way subject to housing shapes. For instance, a concave module housing with flexible extensions embracing about half the circumference of the injection device may be snapped to the device housing. A module housing with two shell-type housing parts that may be releasably locked to each other in the mounted state as disclosed in WO 2011/124633 A1 may also be employed, specifically to engage an injection device with a convex device housing shape. In these cases the circumferential induction coils described above may be replaced by tangential induction coils arranged on a curved, e.g. cylindrical, surface that is coaxial with the main axis, and matching the shape, of the device housing.

In the context of healthcare data management, it is advisable to treat monitoring data that has been collected by any kind of smart monitoring unit, including but not limited to the electronic unit according to the present invention, as Protected Health Information (PHI). In order to avoid data abuse, misappropriation, manipulation or the like to the detriment of the patient or a healthcare provider, several measures may be envisaged. In the following patient adherence data is referred to as the monitoring data accumulated by the electronic unit, including records of time-stamped injection events, but possibly including a log or transcript of a bidirectional interaction between patient and electronic device, including in particular any feedback or recommendation provided to the user. Communication of such patient adherence data from a mobile device or end-user gateway of the user to a remote site has to guarantee privacy and integrity of the data. Specifically, communications containing PHI or equivalent patient adherence data and transmitted electronically over open networks have to be encrypted and protected from being intercepted by anyone other than the intended recipient. Likewise, information technology systems receiving PHI must be protected from intrusion, and the identity of the intended recipient must be authenticated. Data integrity on the other hand may be increased by means of check sum, double-keying, message authentication, and digital signature.

One option for storing patient adherence data in a computing cloud or other distributed data server structure comprises storing the data, on the one hand, in an encrypted format that restricts access to a holder of a particular key. On the other hand, data may be stored as anonymized cloud data, such that the patient may not be identified from the data. Anonymizing data may include location fuzzing, noise addition, permutation, k-anonymization, l-diversity, or similar, and enable analysis of aggregated anonymized but otherwise unencrypted data by research institutions or health care stakeholders. In addition, personally identifiable patient adherence data may be shared directly with a trusted named doctor using standard public-key cryptography.

Another option for storing patient adherence data in a computing cloud comprises uploading personally identifiable patient adherence data to the cloud where it is stored. Data transfer over networks is fully encrypted, and the stored data is accessible for detailed analysis by trusted experts (e.g., cloud-based doctor analysis). This option provides maximum flexibility with regards to analysis of personal data, and enables patients to use a web-based interface to access their data.

A third option enabling a specialized healthcare data service provider to analyze PHI without violating the privacy of the patient resides on encrypting the patient adherence data according to a homomorphic encryption scheme, and sending the encrypted data to a data service provider. The latter may then evaluate the encrypted data and derive, or calculate, encrypted statistical or otherwise augmented information there from. The encrypted information is sent back to a trusted doctor of the patient, or to the end-user gateway embodying some medical expert knowledge, where it is decrypted and used for a refined diagnosis and/or adapted therapy. Fully homomorphic encryption schemes are compatible with an arbitrary number of additions and multiplications on encrypted data. Thus, all data processing functions comprising polynomial operations, including statistical functions such as the mean, standard deviation and logistical regressions, are compatible with homomorphic encryption schemes, and may be utilized by the healthcare data service provider.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims shall not preclude the existence of further meaningful combinations of these elements or steps.

LIST OF REFERENCE NUMERALS 1 injection device
10 device housing
10a window
11 cover sleeve
12 needle protective cap
13a syringe
13b needle
14 cover sleeve spring
14a, 14b first, second cover sleeve spring base
15 end-click element
16 injection spring
2 electronic module
20 module housing
20a opening
20b, 20c upper, lower cover
21 sensor sleeve
21a, 21b recess
22a, 22b first, second sensor induction coil 23a electronic assembly
23b connection detection switch
23c connection status indicator
23d system status indicator
24a locking element
24b locking spring
24c release button
24d release button ring
24e release button ring guide
25 magnetic shield
31 mobile device, smartphone
32 data server, expert system
40 transmitted signal
42 user
5a, 5b, 5c injection events

What is claimed is:

1. A system comprising:
an injection device with a device housing for a filled syringe, the injection device comprising a conductive component at least partially made of electrically conductive material permitting the flow of an alternating current that produces a magnetic field; and
an electronic module with a module housing, the electronic module being adapted to be removably attached to the injection device for monitoring of an injection process executed by the injection device, the injection process comprising administering a drug from the filled syringe,
wherein the electronic module comprises a sensor for detecting during the monitoring, in an attached state of the electronic module and the injection device, electromagnetic changes caused by a two-way displacement of the conductive component, including a first displacement of the conductive component of the injection device from a first to a second component position and by a second, return displacement of the conductive component from the second component position to essentially the first or, in case of injection abort or interruption, to another final component position.

2. The system according to claim 1, wherein the sensor comprises an inductive sensor that comprises an induction coil and the conductive component comprises a metallic spring, metallic shield or other metallic component of the injection device.

3. The system according to claim 2, wherein the induction coil surrounds the injection device in a sensor plane perpendicular to a main axis of the injection device, or the induction coil is arranged on a planar or curved surface coaxial with the main axis.

4. The system according to claim 2, wherein the electronic module comprises a magnetic shield for shielding the inductive sensor against electromagnetic sources other than the displaced conductive component.

5. The system according to claim 1, wherein the injection device comprises:
a cover sleeve movable between a first cover sleeve position in which the cover sleeve surrounds a needle of the injection device and a second cover sleeve position in which the cover sleeve exposes the needle, and
a cover sleeve spring having a first base coupled to the cover sleeve, wherein the conductive component comprises the first base of the cover sleeve spring, and the inductive sensor comprises a first inductive sensor with a first induction coil adapted to detect:
a first displacement of the first base of the cover sleeve spring corresponding to a retracting movement of the cover sleeve between the first cover sleeve position and the second cover sleeve position; and
a second displacement of the first base of the cover sleeve spring corresponding to a forward movement of the cover sleeve from the second cover sleeve position toward the first cover sleeve position.

6. The system according to claim 5, wherein the injection device comprises an End-of-Injection (EoI) signaling assembly comprising a resilient member and an end-click member, wherein the conductive component comprises a member of the EoI signaling assembly, and the inductive sensor comprises a second inductive sensor with a second induction coil adapted to detect a preparatory movement of the EoI signaling assembly and a signaling movement of the EoI signaling assembly.

7. The system according to claim 6, wherein the cover sleeve spring has a second base coupled to the end-click member, and wherein the conductive component comprises the second base of the cover sleeve spring, and the second induction coil is adapted to detect a first displacement of the second base of the cover sleeve spring corresponding to the preparatory movement of the EoI signaling assembly, and a second displacement of the second base of the cover sleeve spring corresponding to the signaling movement of the EoI signaling assembly.

8. The system according to claim 1, wherein the electronic module comprises a status indicator for indicating a status of the system to a user or for indicating a lapse of a holding time.

9. The system according to claim 1, wherein the electronic module comprises a locking mechanism for releasably locking the electronic module axially relative to the injection device.

10. The system according to claim 1, wherein the device housing is elongate and the electronic module housing has a cavity adapted to the device housing and surrounding, in the attached state, at least one half of a length of the injection device.

11. The system according to claim 1, wherein the electronic module comprises a locking mechanism for releasably locking the electronic module axially relative to the injection device, said locking mechanism comprising a protrusion engaging with a counterpart recess of the device housing, wherein the protrusion is biased into locking by means of a locking spring and connected to a release button by a release button ring.

12. The system according to claim 1, wherein the second, return displacement of the conductive component is from the second component position to the final component position, driven under the force of an expanding cover sleeve spring.

13. An electronic module with a module housing, the electronic module being adapted to be removably attached to an injection device comprising a device housing for a filled syringe and a component at least partially made of electrically conductive material, the electronic module configured for monitoring of an injection process comprising a drug injection into a patient from the filled syringe, wherein the module housing comprises a cavity adapted such that, in an attached state of the electronic module and the injection device, the electronic module surrounds the injection device and wherein the electronic module comprises an inductive sensor comprising an induction coil and a sensor control unit for detecting, during the attached state and when monitoring the injection process, an inductance of the induction coil that changes depending on a two-way component displacement of the component of the injection device at least partially made of electrically conductive material.

14. The electronic module of claim 13, wherein the sensor control unit as part of the monitoring is configured to determine the changes in the inductance of the induction coil caused by a first displacement of the conductive component of the injection device from a first to a second component position and by a second, return displacement of the component from the second component position to essentially the first or, in case of injection abort or interruption, to another final component position.

15. The electronic module according to claim 14, wherein the electronic module is configured to determine, based on processing by the sensor control unit of sensor output signals indicative of the first displacement and the second, return displacement of the component, whether or not a correct execution of the injection process occurred.

16. The electronic module according to claim 14, further comprising:
the sensor control unit being configured to produce digital sensor output signals from changes in the inductance of the induction coil; and
an evaluation unit for processing of digital sensor output signals of the sensor control unit indicative of the first displacement and the second, return displacement, and determining whether or not a correct execution of the injection process occurred.

17. The electronic module according to claim 16 further comprising a connection detection switch configured to detect connection of the electronic module for monitoring the injection device and adapted to act as an activation element for activating the electronic module from a power saving mode and/or defining suitable measurement windows for sensor output signals of the inductive sensor, and starting or ending with a connect status as determined by the connection detection switch.

18. The electronic module according to claim 14 wherein the inductive sensor comprises first and second inductive sensors, each comprising an induction coil, and wherein each of the induction coils is adapted to be inductively coupled to a conductive base winding loop of a first base or of a second base of a cover sleeve spring of the injection device.

19. The electronic module according to claim 13, wherein the electronic module comprises a data storage unit with stored data for at least timing and quality information of an injection event monitored, and a wireless communication unit for transmitting the stored data to a mobile device.

* * * * *